United States Patent
Ramsey et al.

[11] Patent Number: 5,913,862
[45] Date of Patent: Jun. 22, 1999

[54] UMBILICAL CORD CUTTING AND CLAMPING DEVICE

[75] Inventors: James Ramsey, 23111 Marvilla La., Coto de Caza, Calif. 92679; Gregg E. Plambeck, 2868 Via Bellota, San Celmente, Calif. 92673; Fernando Suarez, Costa Mesa, Calif.

[73] Assignees: James Ramsey, Cot de Caza; Gregg E. Plambeck, San Clemente, both of Calif.

[21] Appl. No.: 08/846,074

[22] Filed: Apr. 25, 1997

[51] Int. Cl.$^6$ .................................................. A61B 17/12
[52] U.S. Cl. ............................................ 606/120; 606/157
[58] Field of Search ............................ 606/120, 1, 119, 606/138, 139, 142, 151, 157, 167, 205, 207, 208

[56] References Cited

U.S. PATENT DOCUMENTS

| | | | |
|---|---|---|---|
| 3,106,919 | 10/1963 | Churchville | 128/346 |
| 3,171,184 | 3/1965 | Posse | 606/120 |
| 3,323,208 | 6/1967 | Hurley, Jr. | 30/124 |
| 3,361,858 | 1/1968 | Ersek | 128/318 |
| 3,766,925 | 10/1973 | Rubricius | 606/120 |
| 4,026,294 | 5/1977 | Mattler | 128/305 |
| 4,716,886 | 1/1988 | Schulman | 128/305 |
| 4,781,188 | 11/1988 | Collins | 128/305 |
| 4,856,517 | 8/1989 | Collins | 128/346 |
| 4,938,215 | 7/1990 | Schulman | 606/120 |
| 5,009,657 | 4/1991 | Cotey | 606/120 |
| 5,190,556 | 3/1993 | Hessel | 606/120 |
| 5,415,665 | 5/1995 | Hessel | 606/120 |
| 5,462,555 | 10/1995 | Bolanos | 606/120 |
| 5,520,699 | 5/1996 | Hessel | 606/120 |
| 5,575,795 | 11/1996 | Anderson | 606/120 |
| 5,584,840 | 12/1996 | Ramsey | 606/120 |
| 5,667,516 | 9/1997 | Allen | 606/120 |
| 5,676,672 | 10/1997 | Watson et al. | 606/120 |

*Primary Examiner*—Richard J. Apley
*Assistant Examiner*—Benjamin K. Koo
*Attorney, Agent, or Firm*—David P. Gordon; David S. Jacobson; Thomas A. Gallagher

[57] ABSTRACT

An umbilical cord cutting and clamping device includes two clamps abutted in a side-by-side relation and a blade connected to an arm of one of the clamps and positioned between the two clamps. Both clamps have an upper arm and a lower arm, and a hinge coupling the proximal ends of the upper and lower arms. The clamps are held in relative position by frictional engagement and by a latch means which is automatically disengaged when the clamps are moved into a closed position. Both the upper and lower arms include clamping surfaces for clamping the umbilical cord. The proximal end of one of the clamping surfaces is provide with a retention tab which retains the umbilical cord between the clamping surfaces; i.e., the tab prevents the cord from migrating proximally off the clamping surfaces and into the hinge area. The distal portions of the lower arms of the clamps include substantially vertical portions having ratchet surfaces having a plurality of proximally directed teeth which are engaged by a ratchet engagement means at the distal ends of the upper arms. The blade includes a cutting edge which is preferably angled distally downward relative to the upper arms. As the clamps are closed around a section of umbilical cord and clamp the cord, the blade extends between the clamping surfaces and cuts the cord, and the latch means is disengaged. The two clamps are separated from their friction fit while clamping the severed ends of the cord.

29 Claims, 7 Drawing Sheets

UMBILICAL CORD CUTTING AND CLAMPING DEVICE

This application is related to co-owned U.S. Pat. No. 5,584,840, which is hereby incorporated by reference herein in its entirety.

BACKGROUND OF THE INVENTION

1. Field of the Invention

This invention relates broadly to umbilical cord clamps. More particularly, this invention relates to umbilical cord clamps which both sever and clamp the umbilical cord.

2. State of the Art

The umbilical cord serves as the conduit between a mother and a fetus developing in the womb of the mother. Nutrients and oxygen within the blood of the mother pass through the umbilical cord to the fetus. Immediately after a baby is born, the umbilical cord must be clamped to stop the flow of blood therethrough and the cord must then be severed to separate the baby from the placenta. For many years, this procedure utilized two separate clamps to clamp the cord, and a scalpel to cut the cord.

Over the past thirty years, a number of devices have been proposed for both clamping and cutting the cord in an abbreviated procedure, although few of them have been used commercially. For example, U.S. Pat. No. 3,323,208 to Hurley, Jr. shows an umbilical cord clamping device which includes two clamps held in side-by-side positioning by pins on one clamp which frictionally fit into holes on an abutting edge of the other clamp. A blade is positioned between the clamps and cuts the cord as the clamps are closed on the cord. However, the short pins of the clamps do not reliably hold the clamps together such that accidental separation is prevented.

U.S. Pat. No. 3,631,858 to Ersek discloses another cutting and clamping device. The device includes two clamps held together side-by-side by a frangible connector. A cutting blade is coupled to one of the arms of a clamp such that when the clamps are closed on an umbilical cord, the blade first severs the cord and then breaks the connector, thereby separating the clamps. However, the device is somewhat difficult to operate, due to the high force necessary to break the connector.

U.S. Pat. No. 4,026,294 to Mattler shows an umbilical cord clamping device that includes two clamps attached by a frangible connection to the cutting blades of a scissors-like applicator device. Initial squeezing of the handles of the applicator device closes the clamps around the umbilical cord. Further squeezing breaks the connectors to separate the clamps from the cutting blades. However, this device is relatively complicated to set up and use, and requires many parts, including a separate relatively expensive installation device.

U.S. Pat. No. 4,716,886 to Schulman et al. shows a device having two clamps held side-by-side with a shear pin, and a blade slidably positioned between arms of the clamps. The movement of the blade between the arms is impeded by the shear pin. The clamps are closed upon an umbilical cord by pressing the blade downwardly. After the clamps are fully closed, the shear pin is broken by further pressure upon the blade, so that the blade is moved inwardly to sever the umbilical cord. However, the device is difficult to operate, due to the need to break the shear pin. Another more recent patent to Schulman et al., U.S. Pat. No. 4,938,215, discloses a similar device.

U.S. Pat. No. 4,781,188 to Collins discloses an umbilical cord clamping and cutting device that includes two spaced apart clamps positioned within clamping applicator. Closing the applicator simultaneously closes the clamps. A blade is attached to one arm of the applicator, such that when the clamps are simultaneously closed on the cord, the blade automatically cuts the cord. The applicator is then opened and separated from the clamps which remain closed over the severed ends of the cord. The device uses a relatively large number of parts.

U.S. Pat. No. 4,856,517 to Collins et al. discloses a similar device that includes two clamps positioned within an applicator. The clamps are locked in a closed position about an umbilical cord by a latch. A knob having a blade is fitted within a slot in the applicator and is manually moved forward to sever the cord with the blade. When the knob reaches the end of the slot, the latch is engaged and released by the knob to allow the opening and removal of the applicator, leaving the clamps fixed around the umbilical cord. The device requires two steps to operate; first, clamping the cord and, second, moving the blade. Furthermore, the device has a relatively large number of parts, making manufacture of the device relatively expensive.

Each of the above patents pose serious drawbacks in their use and manufacture. First, as discussed above, many require the use of multiple steps, and/or are difficult to operate, and/or require the breaking of pins or frangible connections, and/or require the use of application devices. Second, the devices tend to have a large number of parts, making their manufacture expensive and complex.

Co-owned U.S. Pat. No. 5,584,840 to Ramsey et al. proposes a solution to the shortcomings of previous devices. Ramsey et al. discloses a device including two clamps friction fit in a side-by-side abutting relation, with a blade coupled between the clamps. Each clamp includes a molded outer guard. Using only two fingers of a practitioner, the arms of the clamps may be brought toward each other, such that the guards enclose and hold fast a section of umbilical cord, the blade projects into a space between the two clamps severing the cord, and the interior serrated surfaces of the clamps provide clamping action. After the cord is clamped and severed, the two clamps may be easily separated using the same hand which operated to close the device, with one clamp remaining on the umbilical cord of the infant and the second clamp with blade attached being discarded along with the placenta. The Ramsey et al. device is not only easy to operate, but is very easy and inexpensive to manufacture as it comprises only two molded clamps and a blade.

Though the device of Ramsey et al. offers significant improvements over the prior art, clinical tests suggest that the stability of the device is not ideal during the cutting process.

SUMMARY OF THE INVENTION

It is therefore an object of the invention to provide an umbilical cord cutting and clamping device which is easy to operate.

It is another object of the invention to provide an umbilical cord cutting and clamping device which cuts and clamps in a single motion.

It is a further object of the invention to provide an umbilical cord cutting and clamping device which includes separable clamps which do not inadvertently separate.

It is an additional object of the invention to provide an umbilical cord cutting and clamping device which retains the clamps in a side-by-side arrangement prior to cutting and clamping and which automatically releases after cutting and clamping.

Another object of the invention is to provide an umbilical cord cutting and clamping device which stabilizes the umbilical cord on the clamping surfaces during cutting.

A further object of the invention is to provide an umbilical cord cutting and clamping device which substantially vertically cuts through the umbilical cord regardless of the location on the clamping surfaces of the umbilical cord.

In accord with these objects which will be discussed in detail below, an umbilical cord cutting and clamping device is provided. Generally, the device includes two clamps abutted in a side-by-side relation and a cutting blade connected to an arm of one of the clamps and positioned between the two clamps. Both clamps have an upper arm and a lower arm, and a hinge coupling the proximal ends of the upper and lower arms. The clamps are held in relative position by frictional engagement and by a latch means which is automatically disengaged when the clamps are moved into a closed (clamped) position. Both the upper and lower arms include clamping surfaces for clamping the umbilical cord and between which the blade extends as the clamps are moved into a closed position. The proximal end of one of the clamping surfaces is provide with a substantially vertical retention tab which retains the umbilical cord between the clamping surfaces; i.e., the tab prevents the cord from migrating proximally off the clamping surfaces and into the hinge area. The blade includes a cutting edge which is preferably angled distally downward relative to the upper arms. The distal portions (away from the hinge) of the lower arms of the clamps include substantially vertical portions having ratchet surfaces having a plurality of proximally directed teeth which are engaged by distally directed ratchet engagement means at the distal ends of the upper arms.

As the clamps are closed around a section of umbilical cord and clamp the cord, the blade extends between the clamping surfaces and cuts the cord, and the latch means is disengaged such that the two clamps may be easily separated from their friction fit while clamping the severed ends of the cord. In addition, the relative angle of the cutting edge allows the blade to cut the umbilical cord at approximately the same relative angle between the upper arms and the lower arms regardless of where the cord sits between the clamping surfaces.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
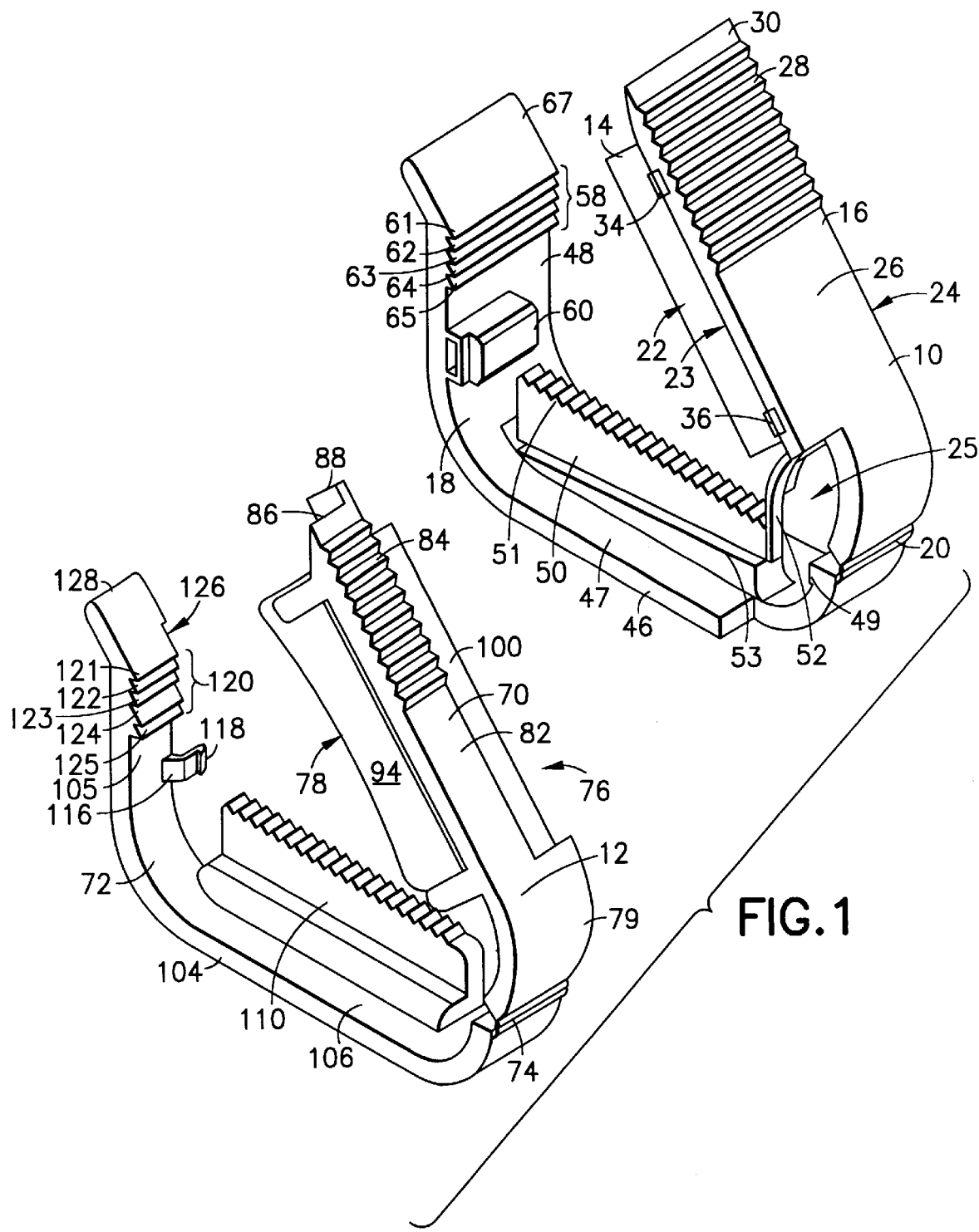
FIG. 1 is a first perspective view of an umbilical cord cutting and clamping device according to the invention in a separated condition.
Figure 2:
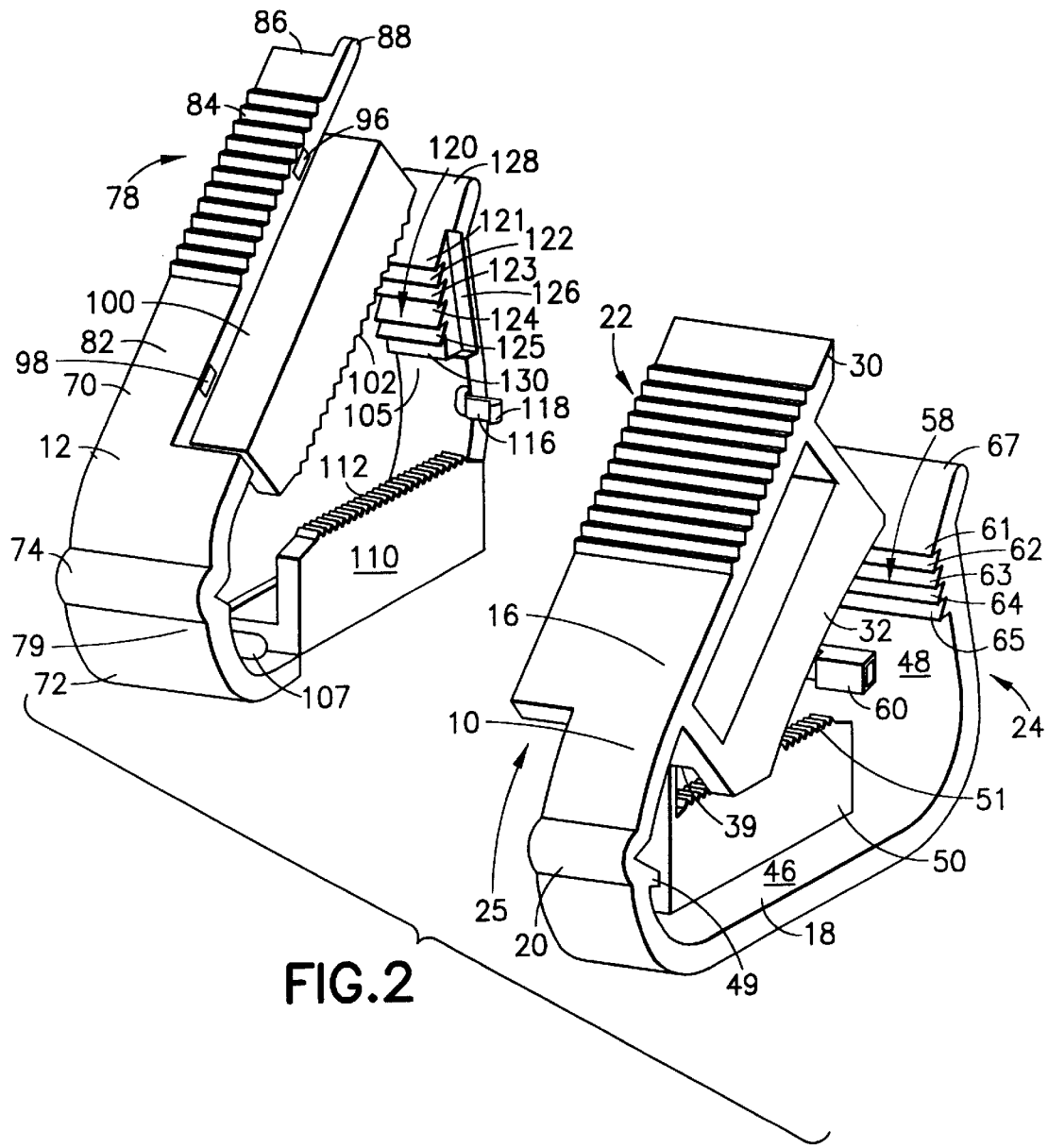
FIG. 2 is a second perspective view of the umbilical cord cutting and clamping device of FIG. 1 in a separated condition.
Figure 3:
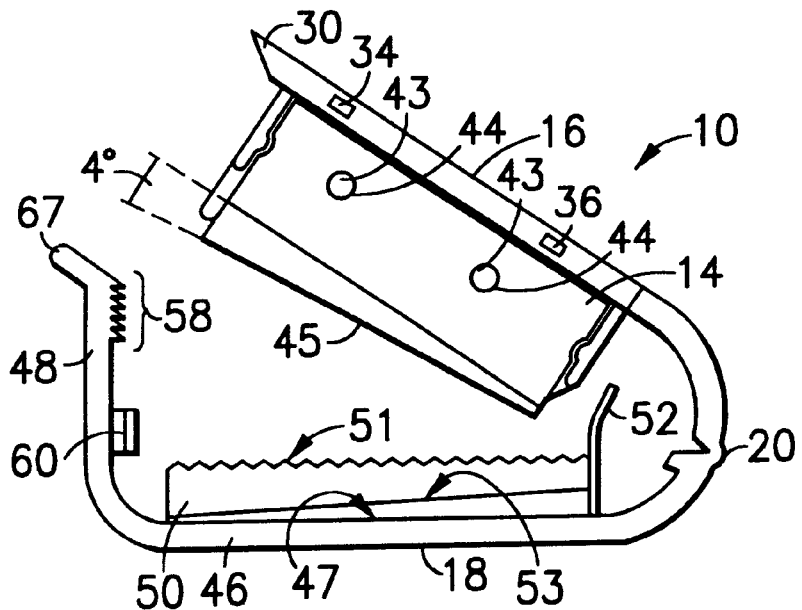
FIG. 3 is a medial side elevation of a first clamp of the umbilical cord cutting and clamping device of FIGS. 1 and 2 in an open position.

Turning now to FIGS. 1 and 2, the umbilical cord cutting and clamping device of the invention is seen to generally include a first clamp 10 and a second clamp 12 which are held in a side-by-side abutting relation, as described in detail below, and a blade 14 coupled to the first clamp 10 and extending between the two clamps. More particularly, with reference to FIGS. 1 through 3, the first clamp 10 includes an upper arm 16, a lower arm 18, a proximal preferably live hinge 20 coupling the upper and lower arms, a medial side 22, and a lateral side 24. Both the upper arm 16 and lower arm 18 are provided at their proximal ends with a cut-out 25 which facilitates coupling the first clamp 10 to the second clamp 12, as described below.

Figure 8:
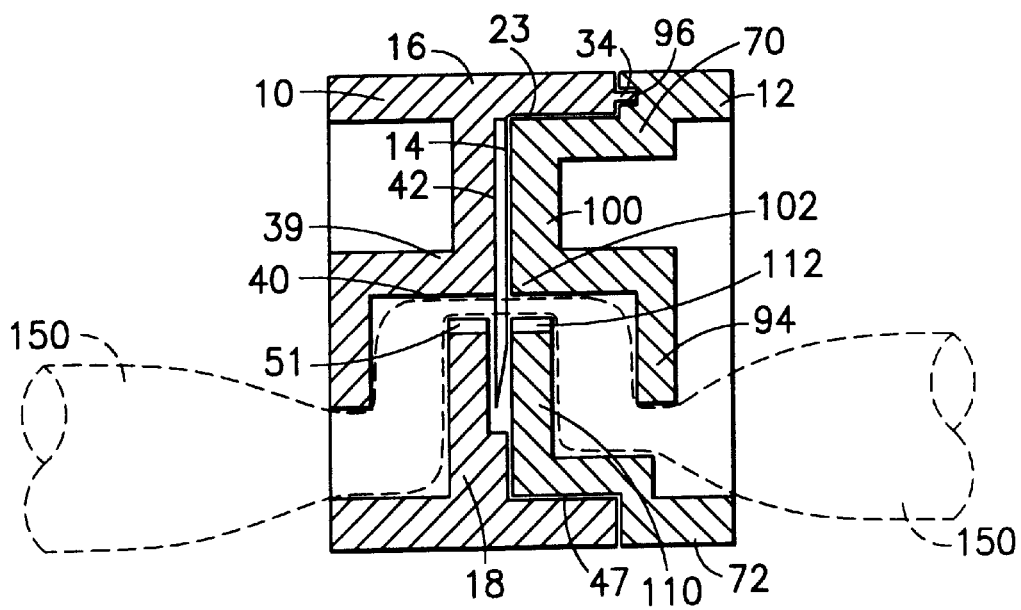
FIG. 8 is a cross-section through line 8—8 in FIG. 7.

The upper arm 16 includes an interior surface 23, a top surface 26 having a serrated portion 28 which facilitates engagement by a human thumb, and an acutely angled distal edge 30 (i.e., ratchet engagement means) for engaging a ratchet surface 58 on the lower arm 18, described below. The lateral side 24 of upper arm 16 preferably is provided with a guard 32. The medial side 22 of the upper arm preferably is provided with lateral protrusions 34, 36 which engage slots 96, 98 in the second clamp 12, also described below. Referring briefly to FIG. 8, the upper arm 16 further includes an upper clamping block 39 having a clamping surface 40, which is preferably serrated with serrations 41 (see FIG. 6), and an inner medial face 42 having two protrusions 43 which fit through holes 44 in the blade 14 and thereby couple the blade to the upper arm (see FIG. 3). Still referring to FIG. 3, the blade is provided with a cutting edge 45 which is preferably angled distally downward between approximately four to fifteen degrees relative to the upper arm 16.

Figure 4:
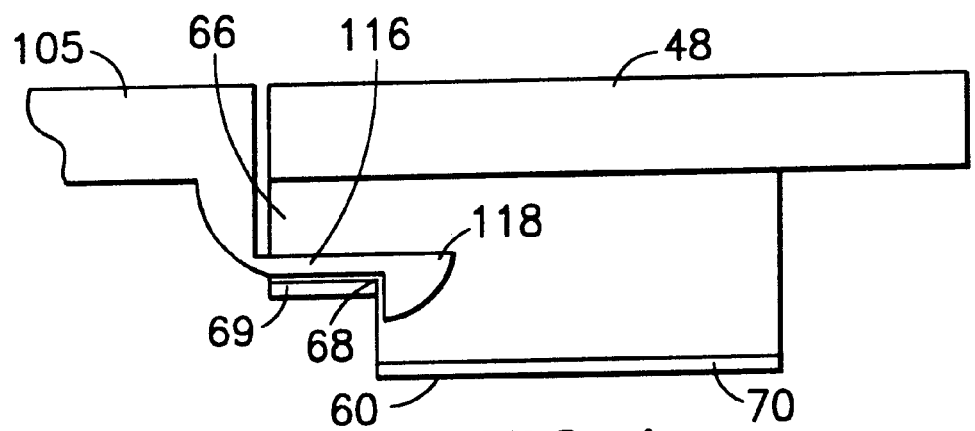
FIG. 4 is a greatly enlarged broken top elevation view of the lateral latch means of the umbilical cord cutting and clamping device of FIGS. 1 and 2 in a locked position.

Turning back to FIGS. 1 through 3, the lower arm 18 of the first clamp 10 includes a substantially horizontal portion 46 with an interior surface 47, and a substantially vertical distal portion 48. The horizontal portion 46 includes a proximal shoulder 49, a lower clamping block 50 having a preferably serrated clamping surface 51, and a blade stop 53. The blade stop 53 is preferably angled at the same relative angle as the cutting edge 45, such that the cutting edge seats flush against the blade stop when the clamp is in a closed position, as described hereinafter. A vertically oriented retention tab 52 is located at the proximal end of the lower clamping surface 50 for preventing slippage of the umbilical cord off of the clamping surface and into the hinge 20 area. Preferably the retention tab 52 is curved proximally to prevent interference with the blade 14 when the clamp is being closed. The distal portion 48 of the lower arm 18 includes a lateral catch 60, a ratchet surface 58 having a plurality of proximally directed and preferably downwardly angled teeth 61–65, and a distally projecting clamp release tab 67. Referring to FIG. 4, the lateral catch 60 includes a medial-side entry 66 having an entry surface 69, and a catch shoulder 68. A body 70 is provided as part of catch 60 for stability.

Turning back to FIGS. 1 and 2, the second clamp 12 includes an upper arm 70 and a lower arm 72, a proximal preferably live hinge 74 coupling the upper and lower arms, a medial side 76, and a lateral side 78. Both the upper arm 70 and lower arm 72 are provided at their proximal ends with a medially extending enlarged portion 79 shaped to the dimensions of the cut-out 25 of the first clamp. A proximal lateral tab 107 adjacent the hinge 74 is provided on the lower arm side of the enlarged portion 79 for abutting the proximal shoulder 49 of the lower arm 18 of the first clamp 10.

The upper arm 70 includes a top surface 82 having a serrated portion 84 which facilitates engagement by a human thumb, and an acutely angled distal edge 86 (or ratchet engagement means) for engaging a ratchet surface 120, described hereinafter. The upper arm 70 is also provided with a distal alignment tab 88 for entering a groove 126 (or slot, as described hereinafter) in the lower arm 72 for laterally aligning the upper and lower arms of both clamps 10, 12. The lateral side 78 of upper arm 70 is provided with a guard 94. The medial side 76 of the upper arm 70 is provided with lateral slots 96, 98 which receive and frictionally engage the lateral protrusions 34, 36 of the first clamp 10. An upper clamping block 100 is also provided on the medial side of the upper arm 70, extending medially outward from and below the top surface 82. The upper clamping block 100 includes a preferably serrated clamping surface 102.

The lower arm 72 of the second clamp 10 has a substantially horizontal portion 104 with an upper surface 106, and a substantially vertical distal portion 105. A lower clamping block 110 having a preferably serrated clamping surface 112 is provided along the medial side 76 of the horizontal portion 104 of the lower arm 72. The lower clamping block 110 extends medially outward beyond and parallel the upper surface 106 of the lower arm 72 so that the horizontal portion of the lower arm of the clamp 10 can extend thereunder as discussed hereinafter. The distal portion 105 includes a medially extending latch 116 having a proximally directed barb 118, a ratchet surface 120 having a plurality of proximally directed and preferably downwardly angled teeth 121–125, an alignment groove 126, and a clamp releasing tab 128.

Figure 5:
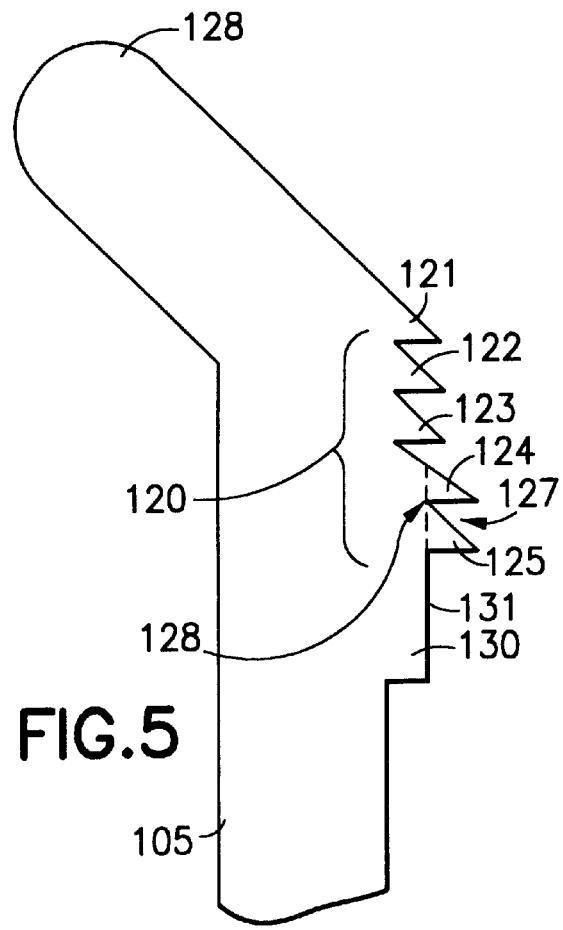
FIG. 5 is a greatly enlarged broken side elevation view of a portion of a ratchet means of the umbilical cord cutting and clamping device of FIGS. 1 and 2.

Referring to FIG. 5, the upper teeth 121–123 of the ratchet surface 120 of clamp 12 are substantially matched in size and downward angle to the teeth 61–65 on the lower arm of the first clamp 10. The lower teeth 124, 125 of clamp 12 are displaced proximally relative to the upper teeth 121–123. A releasing block 130 is preferably provided on the lower arm adjacent and below the lower teeth 124, 125, with the proximal surface 131 of the releasing block 130 being substantially co-planar with the nadir 128 of the trough 127 between the lower teeth 124, 125.

Figure 6:
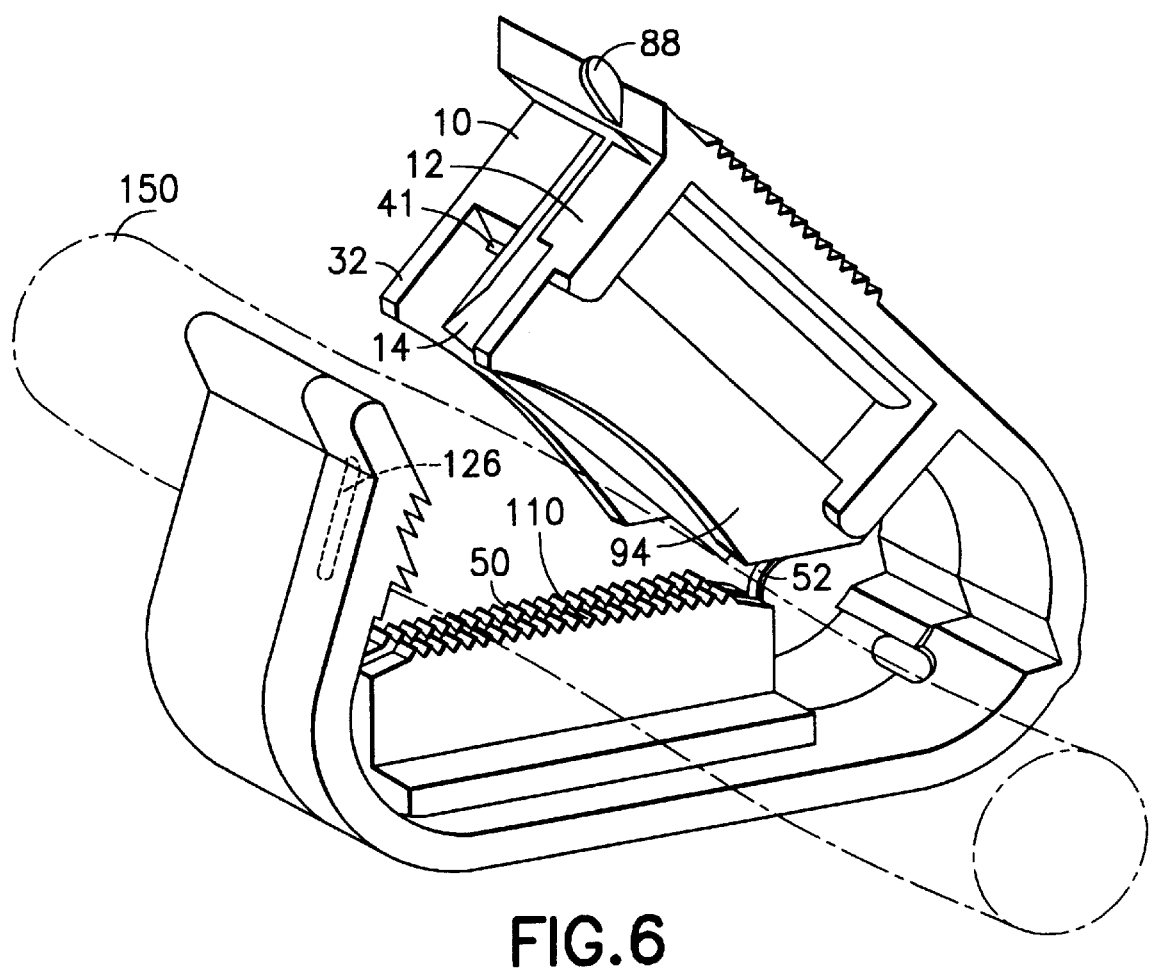
FIG. 6 is a perspective view of the umbilical cord cutting and clamping device of FIGS. 1 and 2 in an open position.

Turning to FIG. 6 in conjunction with FIGS. 1 and 2, the first and second clamps are assembled as an umbilical cord clamping and cutting unit with corresponding elements of the first and second clamps 10, 12 frictionally fit into one another and the latch 116 of the second clamp interlocked in the catch 60 of the first clamp. In particular, the medially extending upper clamping block 100 and lower clamping block 110 of the second clamp are inserted between the upper and lower arms 16, 18 of the first clamp 10 and seat against the interior surfaces 23 and 47 of the upper and lower arms. The protrusions 34, 36 on the upper arm 16 of the first clamp are frictionally fit into the slots 96, 98 on the upper arm 70 of the second clamp. The proximal tab 107 of the enlarged portion 79 of the second clamp seats against the proximal shoulder 49 of the lower arm of the first clamp. As the clamps 10 and 12 are brought together, the barb 118 of the latch 116 is inserted through the medial entry 66 of the catch and the latch is biased distally by contact of the barb 116 against the entry surface 69. Once the barb 118 is inserted beyond the entry surface 69, the latch 116 springs back such that the barb 118 engages the shoulder 68. The medial sides 22, 76 of the first and second clamps seat against each other such that the groove 126 and the medial sides of the distal portion of the lower arms form a slot into which the alignment tab 88 can extend. It will be appreciated that while there are a number of elements which engage each other, assembly of the two clamps into one clamping device is accomplished simply in single motion (preferably during manufacture).

Figure 7:
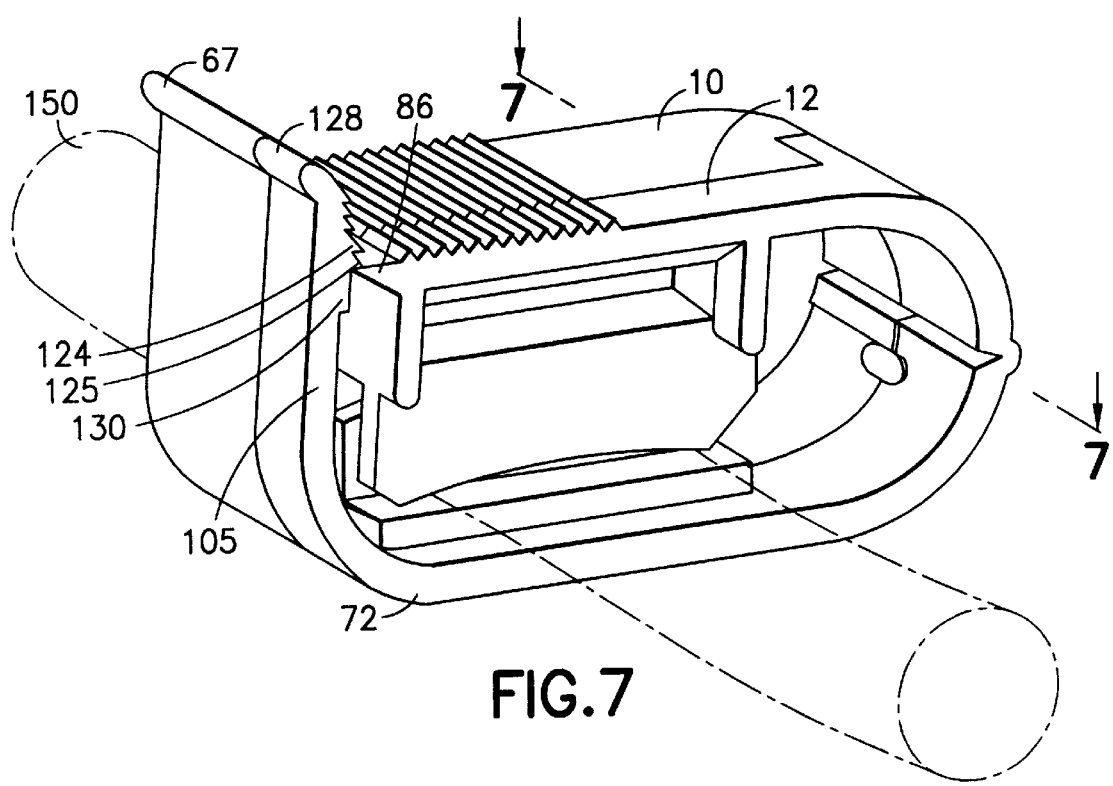
FIG. 7 is a perspective view of the umbilical cord cutting and clamping device of FIGS. 1 and 2 in a closed position.
Figure 9:
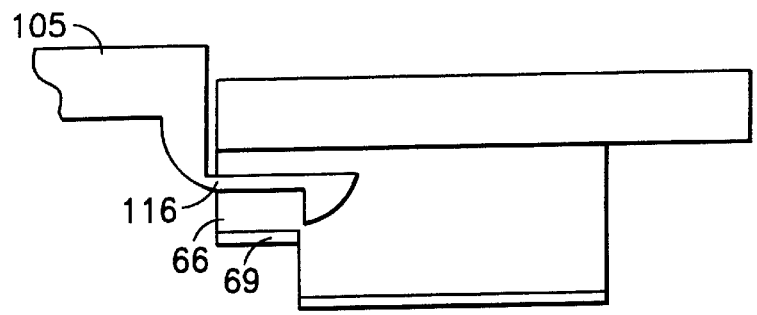
FIG. 9 is a greatly enlarged broken top elevation view of the lateral latch means of the umbilical cord cutting and clamping device of FIGS. 1 and 2 in an unlocked position.
Figure 10:
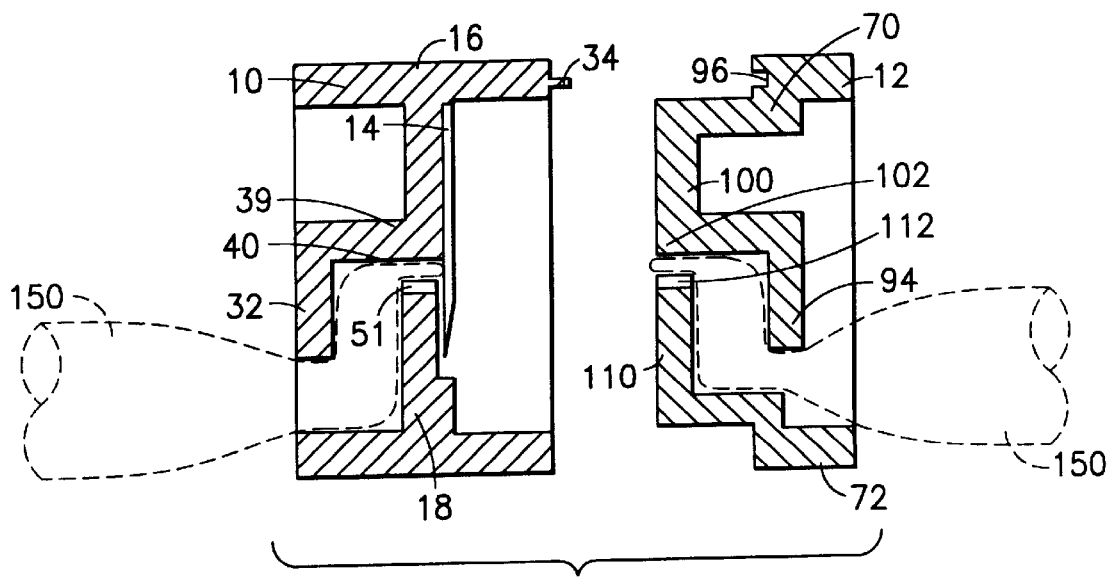
FIG. 10 is a view similar to FIG. 8, with the umbilical cord cutting and clamping device in a separated condition.

Referring to FIG. 4, the device is operated by, first, placing an umbilical cord 150 between the arms of the clamping device, preferably oriented such that the first clamp is on the mother's side of the umbilical cord and the second clamp is on the baby's side of the umbilical cord. The upper and lower arms are next squeezed toward each other such that the guards 32 and 94 force the cord against the lower clamping surfaces 50 and 110 and the cutting edge 45 of the blade 14 begins to cut through the cord. The guards 32, 94 serve the additional purpose of preventing a practitioner's finger from accidentally being caught in the path of the blade 14. In addition, the angular offset of the cutting edge 45 permits the blade to cut through the cord in a seemingly downward motion and, as a result, the blade cuts the umbilical cord at approximately the same relative angle between the upper arms and lower arms regardless of where the cord sits between the clamping surfaces. The proximal retention tab 52 prevents the cord 150 from moving proximally along the clamping surfaces and into the hinged area before and as the cord is being cut. As the upper arms are further squeezed toward the lower arms (from the position of FIG. 6 to the position of FIG. 7), the ratchet engagement means of the upper arms engage the ratchet surfaces of the lower arms; i.e., the distal edges 30 and 86 engage the teeth 61–65 on the first clamp and teeth 121–125 on the second clamp, respectively. In addition, as the upper and lower arms are squeezed toward each other, the alignment tab 88 extends into the slot formed by the juxtaposition of the medial sides of the distal portion of the lower arms and the groove 126, thereby maintaining the clamps in lateral alignment. Referring to FIGS. 7 and 8, as the arms are moved closer together, the clamping surfaces tighten around the cord and the cord is fully severed by the blade. As the ratchet engagement means 86 on the distal end of the second clamp 12 engages the lower teeth 124 and 125, it operates to move the distal portion 105 of the lower arm 72 of the second clamp 12 distally, and to release the barb 118 of the latch 116 from the shoulder 68 of the catch 60 (as shown in FIG. 9). When the second clamp is fully closed (FIG. 7), the ratchet engagement means 86 seats against the releasing block 130 and keeps the latch 116 freely removable from the entry 66 of the catch 60, such that only a friction fit keeps the two clamps 10 and 12 in their side-by-side position. Using the same hand the practitioner used to close the clamping device, the practitioner, using his/her fingers, can easily separate the first and second clamps from their friction fit; i.e., the clamping device may be transformed from the orientation shown in FIG. 8 to the orientation shown in FIG. 10. Once the first and second clamps are separated, the first clamp (with blade), can be discarded, and the second clamp is left to remain, temporarily, on the baby. Turning back to FIG. 7, it will be appreciated that each of the clamps may be opened from a closed position by pushing/pulling distally on the respective release tab 67 and 128.

It will be appreciated that the device includes only three distinct parts, the two clamps and the blade and is therefore easy to manufacture. Moreover, the preferred material for the clamps is a medical grade plastic which can easily and inexpensively be molded to the shape of the clamps, can accommodate a live hinge, and can preferably be provided with a gamma inhibitor such that the material is gamma stable. For example, polypropylene, nylon, and high density polyethylene are all suitable materials.

There have been described and illustrated herein an umbilical cord cutting and clamping device. While a particular embodiment of the invention has been described, it is not intended that the invention be limited thereto, as it is intended that the invention be as broad in scope as the art will allow and that the specification be read likewise. Thus, while a particular lateral latching mechanism has been described, it will be appreciated that other lateral latching means may also be used to secure the clamps in a side-by-side relation until the clamps have fully clamped the cord and until the cord is completely severed. In addition, while the upper and lower arms of each clamp are preferably coupled by a live hinge, it will be appreciated that other hinges may be used as well. Furthermore while it is preferable to have guards on the lateral sides of the clamps for engaging the cord and for protecting the fingers of the practitioner, it will be appreciated that the guards are not necessary and that the clamp will fully function without the guards. Moreover, while the retention tab is described as being located adjacent the clamping surface on the lower arm of the first clamp, it will be appreciated that it may be located elsewhere (on the second clamp or on the upper arm) and still perform the same function. Also, while the blade is shown preferably coupled to the first clamp, it will be recognized that the blade may alternatively be coupled to the second clamp. In addition, while the blade is shown connected to the upper arm of the first clamp, it may alternatively be connected to a lower arm. Moreover, while a particular configuration has been disclosed in reference to elements which are friction fit to one another to hold the two clamps in a side-by-side configuration, it will be appreciated that other elements in a similar or different configuration could be used as well. Also, while five teeth are shown on the ratchet surface, fewer or more teeth may be provided; in addition, fewer or more upper and/or lower teeth may also be provided. In addition, while the teeth are shown angled downward, it will be appreciated that they need not be. Furthermore, while a slot is shown formed by a groove between the two clamps, it will be appreciated that the slot may be formed elsewhere. Moreover, while the entry surface 69 is shown to be substantially parallel to the vertical distal portion of the lower arm of the first clamp, it will be appreciated that the entry surface may be provided at an angle relative to the distal portion. Also, while the cutting edge of the blade and blade stop have been shown to have an angular offset relative to the upper arm, it will be appreciated that no angular offset need be provided. Furthermore, where an angular offset is provided, rather than angle the cutting edge relative to the opposite side of the blade to provide the offset, it will be appreciated that the entire blade may be angularly offset relative to the upper arm. In addition, while medical grade plastic is the preferred material for manufacture, it will be understood that metal or other suitable materials can be similarly used. It will therefore be appreciated by those skilled in the art that yet other modifications could be made to the provided invention without deviating from its spirit and scope as so claimed.

We claim:

1. An umbilical cord cutting and clamping device, comprising:

a) a first clamp having a first upper arm and a first lower arm;

b) a second clamp having a second upper arm and a second lower arm;

c) a latch means oriented perpendicular to said first lower arm and said second lower arm for laterally disengageably coupling said first clamp to said second clamp in a side-by-side relation, said latch means including interengaging elements on said first and second clamps, at least one of said interengaging elements being resilient, said latch means automatically disengaging said first clamp from said second clamp when said cutting and clamping device is moved substantially towards a closed position; and d) a blade coupled to one of said first clamp and said second clamp.

2. An umbilical cord cutting and clamping device according to claim 1, wherein:

said first lower arm and said second lower arm include first and second distal portions, respectively, and movement of said first distal portion distally relative to said second distal portion causes said latch means to automatically disengage said first clamp from said second clamp.

3. An umbilical cord cutting and clamping device according to claim 2, wherein:

said latch means includes a latch on said first distal portion, said latch being provided with a barb, and a catch means on said second distal portion for receiving said latch.

4. An umbilical cord cutting and clamping device according to claim 3, wherein:

said catch means include a latch entry which receives said barb, an entry surface which guides said barb, and a shoulder which retains said barb, said latch being biased such that said barb, once inserted into said latch entry, seats against said shoulder, and such that moving said first distal portion distally relative to said second distal portion releases said barb from said shoulder.

5. An umbilical cord cutting and clamping device according to claim 1, wherein:

said first clamp includes locking means to lock said first upper arm relative to said first lower arm when said cutting and clamping device is in the closed position such that said first clamp is in a locked position.

6. An umbilical cord cutting and clamping device according to claim 5, wherein:

said locking means is a ratchet on said first lower arm and a ratchet engaging means on said first upper arm.

7. An umbilical cord cutting and clamping device according to claim 5, wherein:

said first clamp includes a releasing means for releasing said locking means.

8. An umbilical cord cutting and clamping device according to claim 7, wherein:

said releasing means is a tab.

9. An umbilical cord cutting and clamping device according to claim 1, wherein:

said first upper arm includes an alignment tab and said first lower arm at least partially defines a groove which receives said alignment tab.

10. An umbilical cord cutting and clamping device according to claim 1, wherein:

said first upper arm, said first lower arm, said second upper arm, and said second lower arm are each provided with a clamping surface, and at least one of said first upper arm, said first lower arm, said second upper arm, and said second lower arm includes an umbilical cord retention means for preventing the cord from migrating proximally from between said clamping surfaces.

11. An umbilical cord cutting and clamping device according to claim 1, wherein:

said blade has a straight cutting edge which is angled relative to a longitudinal axis of a portion of said one of said first clamp and said second clamp to which said blade is coupled.

12. An umbilical cord cutting and clamping device, comprising:

a) a first clamp having a first upper arm and a first lower arm, said first lower arm having a first portion and a distal portion angled relative to said first portion said distal portion being provided with a ratchet having a plurality of substantially proximally directed teeth and said first upper arm having a distally directed ratchet engagement means for engaging said plurality of teeth, said plurality of proximally directed teeth including at least one upper tooth and at least one lower tooth vertically displaced below and proximally displaced relative to said at least one upper tooth;

b) a second clamp having a second upper arm and a second lower arm;

c) means for coupling said first clamp to said second clamp in a side-by-side relation; and d) a blade coupled to one of said first clamp and said second clamp, wherein, in a locked position, said ratchet engagement means engages at least a first of said plurality of proximally directed teeth.

13. An umbilical cord cutting and clamping device according to claim 12, wherein:

said distal portion is provided with a clamp releasing tab, wherein, in a locked position, said clamp releasing tab is engaged to move said distal portion distally relative to said ratchet engagement means and to thereby release said first clamp to an unlocked position.

14. An umbilical cord cutting and clamping device according to claim 12, wherein:

said second lower arm has a second distal portion provided with a second ratchet having a second plurality of proximally directed teeth and said second upper arm has a second distally directed ratchet engagement means for engaging second plurality of teeth, wherein, in a locked position, said second ratchet engagement means engages at least a first of said second plurality of proximally directed teeth.

15. An umbilical cord cutting and clamping device according to claim 12, wherein:

said first clamp includes a first hinge connecting said first upper arm to said first lower arm, and said second clamp includes a second hinge connecting said second upper arm to said second lower arm.

16. An umbilical cord cutting and clamping device according to claim 12, wherein:

said ratchet engagement means is an acutely angled distal edge portion of said first upper arm.

17. An umbilical cord cutting and clamping device according to claim 12, wherein:

said coupling means is a latch assembly operating perpendicular to said first lower arm.

18. An umbilical cord cutting and clamping device according to claim 17, wherein:

said latch assembly includes a latch on said distal portion of said first lower arm of said first clamp, said latch being provided with a barb biased to be disengageably engaged in a catch on a second distal portion of said second clamp, wherein moving said distal portion of said first lower arm distally relative to said second distal portion releases said latch from said catch.

19. An umbilical cord cutting and clamping device according to claim 18, wherein:

said distal portion of said first lower arm includes a latch releasing means for engaging said ratchet engagement means when said clamp is in said locked position and for maintaining said distal portion of said first lower arm in a distal position relative to said ratchet engagement means such that said barb is released from said catch, enabling said first clamp to be separated from said second clamp.

20. An umbilical cord cutting and clamping device according to claim 12, wherein:

said upper arm includes an alignment tab and said lower arm is provided with a groove for receiving said alignment tab.

21. An umbilical cord cutting and clamping device according to claim 12, wherein:

said first upper arm, said first lower arm, said second upper arm, and said second lower arm are each provided with a clamping surface, and at least one of said first upper arm, said first lower arm, said second upper arm, and said second lower arm includes an umbilical cord retaining means for preventing the cord from migrating away from said clamping surfaces.

22. An umbilical cord cutting and clamping device, comprising:

a) a first clamp having a first upper arm and a first lower arm movable relative toward said first upper arm upon closure of said cutting and clamping device;

b) a second clamp having a second upper arm and a second lower arm movable relative toward said second upper upon closure of said cutting and clamping device;

c) a latch means for laterally disengageably coupling said first clamp to said second clamp in a side-by-side relation such that said first clamp and said second clamp are fixed in three dimensions relative to each other when coupled by said latch means, said latch means including interengaging elements on said first and second clamps, at least one of said interengaging elements being resilient; and d) a blade coupled to one of said first clamp and said second clamp.

23. An umbilical cord cutting and clamping device according to claim 22, wherein:

said first lower arm and said second lower arm include first and second distal portions, respectively, and movement of said first distal portion distally relative to said second distal portion releases said latch means such that said first clamp and said second clamp may be uncoupled from said side-by-side relation.

24. An umbilical cord cutting and clamping device according to claim 23, wherein:

said latch means includes a latch on said first distal portion, said latch being provided with a barb, and a catch means on said second distal portion for receiving said latch.

25. An umbilical cord cutting and clamping device according to claim 24, wherein:

said catch means include a latch entry which receives said barb, an entry surface which guides said barb, and a shoulder which retains said barb, said latch being biased such that said barb, once inserted into said latch entry, seats against said shoulder, and such that moving said first distal portion distally relative to said second distal portion releases said barb from said shoulder.

26. An umbilical cord cutting and clamping device according to claim 22, wherein:

said first clamp includes locking means to lock said first upper arm relative to said first lower arm such that said first clamp is in a locked position.

27. An umbilical cord cutting and clamping device according to claim 22, wherein:

said blade has a straight cutting edge which is angled relative to a longitudinal axis of a portion of said one of said first clamp and said second clamp to which said blade is coupled.

28. An umbilical cord cutting and clamping device, comprising:

a) a first clamp having a first upper arm and a first lower arm;

b) a second clamp having a second upper arm and a second lower arm;

c) a latch means for laterally disengageably coupling said first clamp to said second clamp in a side-by-side relation such that said first clamp is fixed in three dimensions relative to said second clamp when said cutting and clamping deice is in an open position, said latch means including a barbed latch on one of said first and second clamps and a catch which receives said barbed latch on the other of said first and second clamps, said latch means for further automatically disengaging said barbed latch from said catch when said cutting and clamping device is moved substantially towards a closed position; and d) a blade coupled to one of said first clamp and said second clamp.

29. An umbilical cord cutting and clamping device, comprising:

a) a first clamp having a first upper arm and a first lower arm movable relative toward said first upper arm upon closure of said cutting and clamping device;

b) a second clamp having a second upper arm and a second lower arm movable relative toward said second upper upon closure of said cutting and clamping device;

c) a latch means for laterally disengageably coupling said first clamp to said second clamp in a side-by-side relation such that said first clamp and said second clamp are fixed in three dimensions relative to each other when coupled by said latch means, said latch means including a barbed latch on one of said first and second clamps and a catch which receives said barbed latch on the other of said first and second clamps, said latch means automatically disengaging said latch from said catch when said cutting and clamping device is moved substantially towards a closed position; and d) a blade coupled to one of said first clamp and said second clamp.

* * * * *